(12) United States Patent
Kiekens et al.

(10) Patent No.: US 9,603,803 B2
(45) Date of Patent: Mar. 28, 2017

(54) PROCESS FOR PREPARING SPRAY DRIED FORMULATIONS OF 4-[[6-AMINO-5-BROMO-2-[(4-CYANOPHENYL)AMINO]-4-PYRIMIDINYL]OXY]-3,5-DIMETHYLBENZONITRILE

(75) Inventors: Filip Rene Irene Kiekens, Geel (BE); Jody Firmin Marceline Voorspoels, Reningelst (BE); Lieven Elvire Colette Baert, Bruges (BE)

(73) Assignee: JANSSEN SCIENCES IRELAND UC, Little Island, Co. Cork (IE)

( * ) Notice: Subject to any disclaimer, the term of this patent is extended or adjusted under 35 U.S.C. 154(b) by 0 days.

(21) Appl. No.: 13/398,400

(22) Filed: Feb. 16, 2012

(65) Prior Publication Data

US 2012/0208834 A1 Aug. 16, 2012

Related U.S. Application Data

(63) Continuation of application No. 12/302,366, filed as application No. PCT/EP2007/055607 on Jun. 6, 2007, now abandoned.

(30) Foreign Application Priority Data

Jun. 6, 2006 (EP) .................................... 06115029

(51) Int. Cl.
*A61K 31/50* (2006.01)
*A61K 47/00* (2006.01)
*A61K 9/16* (2006.01)

(52) U.S. Cl.
CPC .................. *A61K 9/1652* (2013.01)

(58) Field of Classification Search
CPC ............................ A61K 9/1652; A61K 31/505

USPC ................. 514/247, 675, 724, 781
See application file for complete search history.

(56) References Cited

U.S. PATENT DOCUMENTS

| 6,395,303 | B1 | 5/2002 | Staniforth et al. |
| 6,531,158 | B1 | 3/2003 | Teng et al. |
| 2003/0185893 | A1 | 10/2003 | Beyerinck et al. |
| 2005/0129772 | A1 | 6/2005 | Smith et al. |
| 2006/0078609 | A1 | 4/2006 | Vandecruys et al. |

FOREIGN PATENT DOCUMENTS

| WO | WO 0027825 A1 | 5/2000 |
| WO | WO 01/22938 A1 | 4/2001 |
| WO | WO 01/23362 A2 | 4/2001 |
| WO | WO 2005/011702 A1 | 2/2005 |

OTHER PUBLICATIONS

Martindale, The Extra Pharmacopoeia, 29$^{th}$ Edition, Edited by James E. F. Reynolds (1989), pp. 1435-1436.
International Search Report PCT/EP2007/055607, mailed Sep. 12, 2007.
EP Communication of a Notice of Opposition dated Jun. 8, 2012.
Response to the Opposition filed by Teva Pharmaceutical Industries Ltd. filed on May 31, 2012 against EP 2 029 110 B1.
European Opposition Division Decision to Reject Opposition Dated Jan. 7, 2013.
Statement of Grounds of Appeal by Opponent Dated Nov. 11,2013.
EP2029110 Response to Grounds of Appeal, Mar. 28, 2014.
Gennaro R. Alfonso, Remington Farmacia, 19th Edition, Panamericana, Spain, 1988 p. 2517.
Patentability Examination Report No. 2016-52 for Ecuadorian Appln. No. SP 08-8938—PCT dated Oct. 3, 2016.

*Primary Examiner* — Shobha Kantamneni (57) ABSTRACT

This invention relates to a process for producing a spray-dried powder comprising microcrystalline cellulose in a solid dispersion of the anti-HIV compound etravirine (TMC125) in a water-soluble polymer.

9 Claims, 9 Drawing Sheets

PROCESS FOR PREPARING SPRAY DRIED FORMULATIONS OF 4-[[6-AMINO-5-BROMO-2-[(4-CYANOPHENYL)AMINO]-4-PYRIMIDINYL]OXY]-3,5-DIMETHYLBENZONITRILE

CROSS REFERENCE TO RELATED APPLICATIONS

This application is a continuation of pending U.S. application Ser. No. 12/302,366, filed Nov. 25, 2008 now abandoned, which in turn is a national stage of PCT Application No. PCT/EP2007/055607, filed Jun. 6, 2007, which claims priority for EPO Patent Application No. 06115029.8, filed Jun. 6, 2006 all of which are hereby incorporated by reference in their entirety.

This invention relates to a process for producing a spray-dried powder comprising microcrystalline cellulose in a solid dispersion of the anti-HIV compound etravirine (TMC125) in a water-soluble polymer.

It is well known that pharmaceutical agents that are poorly soluble in water suffer from the problem of having low bioavailability. By "bioavailability" is meant the degree to which and the rate at which a pharmaceutical agent is absorbed or becomes available at the site of physiological activity after administration. One consequence of a pharmaceutical agent having low bioavailability is that the amount (or dose) of the agent administered to a patient needs to be higher. However, increasing the dose leads to an increase in the size and/or the number of dosage forms (such as pills, tablets, capsules etc.) required. The number or volume of dosage forms that need to be administered is commonly referred to as the "pill burden".

A high pill burden is undesirable for many reasons, such as the patient not only having to spend more time taking each dose but also to store and/or transport a large number or volume of pills. A high pill burden also increases the risk that patients will not take their entire dose, thereby failing to comply with the prescribed dosage regimen. As well as reducing the effectiveness of the treatment, this may also lead to the disease-causing organism or virus becoming resistant to the pharmaceutical agent. The problems associated with a high pill burden are multiplied where a patient must take a combination of a number of different types of pharmaceutical agents. One example of such a group of patients is that being treated for the human immunodeficiency virus (HIV), which is the virus causing the acquired immunodeficiency syndrome (AIDS). Anti-HIV treatment typically involves the administration of a combination of a number of different pharmaceutical agents.

It is known that bioavailability of poorly soluble active agents can be improved by converting them in amorphous form. Typically, the more crystalline the pharmaceutical agent, the lower is its bioavailability or vice versa, reducing the degree of crystallinity has a positive effect on bioavailability.

One way of converting an active ingredient into an amorphous form is by presenting it in the form of a solid dispersion in a water-soluble polymer. Different types of solid dispersions exist. One type of solid dispersion is where the pharmaceutical agent is molecularly dispersed, substantially homogeneously, throughout the polymer. This is generally described as a "solid solution". Another type of solid dispersion is where there are islands or clusters of crystalline or semi-crystalline pharmaceutical agent dispersed throughout the polymer. A further type of solid dispersion is where there are islands or clusters of pharmaceutical agent in amorphous form dispersed throughout the polymer. There may also be solid dispersions comprising mixtures of two or more of the above types, for example a solid solution with areas where the pharmaceutical agent is crystalline or semi-crystalline, or where there are islands or clusters of the agent in amorphous form. All these types will be commonly designated hereinafter as "solid dispersions".

A number of methods exist for producing solid dispersions of a pharmaceutical agent. One method consists in dissolving the agent and the water-soluble polymer in a solvent in which both are soluble and allowing the solvent to simply evaporate. The resulting dispersion can be further processed, e.g. by milling and converting the resulting powder, optionally after addition of further excipients, into the desired pharmaceutical dosage forms such as by compressing into tablets or filling in capsules.

A further method is melt extrusion involving the incorporation of the poorly water-soluble pharmaceutical agent into a water-soluble polymer by melting or plasticizing the agent and the polymer and subsequently cooling the resulting melt. Rapid cooling of the melt typically results in the production of a solid solution. Typical melt extrusion processes are described in WO 01/22938 and WO 01/23362.

The Würster coating process involves swirling carrier beads in a chamber using a warm or hot gas flow introduced from the bottom of a spray chamber. The polymer and pharmaceutical agent solution is then sprayed into the chamber, from the bottom. In this way, the swirling beads are coated with a layer of solution and, as the solvent evaporates, a solid dispersion of pharmaceutical agent in the polymer is formed as a layer on the carrier beads. The nature of this technique means that it operates as a batch process, and so there is considerable downtime during production while the coated beads are removed and uncoated beads are admitted to the chamber. The size of the carrier beads and the spray conditions, such as gas flow and temperature, evaporation time, chamber type, pressure and humidity, spray rate influence the solid dispersion formation.

Another method involves a spray drying process in which the water-soluble polymer and the poorly water-soluble pharmaceutical agent are dissolved in a solvent that is able to dissolve both ingredients. The resulting solution is sprayed in droplets, or atomized, into a spray-drying chamber from the top, side or bottom (usually from the top) of the chamber into a stream of hot gas. The solvent is evaporated from the droplets of solution and the resulting dry solid dispersion in powdered form is collected, e.g. in a cyclone. The spraying and drying of the solution can be carried out in a number of ways, which determine the properties of the solid dispersion produced. For example, the conditions in the chamber may be selected so that there is a very fast evaporation rate of the solvent, so-called "flash evaporation", which results in the pharmaceutical agent in the powder having a low degree of or no crystallinity, i.e. it is highly amorphous.

Spray-drying is attractive because it is a continuous (as opposed to batch) process applicable at large scale. Typical methods for making spray-dried solid dispersions of pharmaceutical agents are described in WO 01/22938.

A compound that suffers from poor water-solubility and concomitant low bio-availability is the NNRTI known as "TMC125", which is the compound 4-[[6-amino-5-bromo-2-[(4-cyanophenyl)amino]-4-pyrimidinyl]oxy]-3,5-dimethylbenzonitrile, also referred to as Etravirine or R165335. TMC125 can be represented by the formula (I):

(I)

This compound, its properties, a number of synthetic approaches for its preparation as well as standard pharmaceutical formulations have been described in WO 00/27825. TMC125, currently in late stage clinical development, not only shows pronounced activity against wild type HIV, but also against many mutated variants. Converting TMC125 into a solid dispersion, such as by spray-drying, improves its bioavailability.

However, the powder resulting from this spray-drying process is "fluffy" in that it contains a large amount of gas. As such, the resulting fluffy powder has a low density, typically in the region of about 0.1 g/ml. This means that the powder is difficult to compact, which is a problem during its subsequent formulation into dosage forms, such as tablets, pills or capsules. For example, in order to formulate the powder produced by spray-drying into tablet form, a pre-compacting step is usually required, whereby the powder is roller-compacted or slugged in order to increase its density.

Hence there is a need for a process for producing an improved form of a spray-dried solid dispersion of TMC125 having improved bioavailability. There is further need to provide a solid dispersion of TMC125 that may be readily converted into a pharmaceutical formulation or a pharmaceutical dosage form, such as a tablet, pill or capsule, with limited need for additional excipient addition.

It now has been found that the dissolution profile of TMC125 can be improved by adding microcrystalline cellulose, which is also referred to as "MCC", to the mixture that is spray dried. In particular the dissolution speed in aqueous media of the TMC125 active ingredient from a solid dispersion is increased, resulting in higher concentrations of the drug. This may result into higher plasma levels and a quicker onset of the TMC125 active ingredient.

The present invention provides a process for producing a solid dispersion of TMC125 in powder form, or alternatively, the invention provides a process for producing a solid pharmaceutical powder, comprising the steps of:
(a) providing a feed mixture of microcrystalline cellulose and a solution of a water-soluble polymer and TMC125;
(b) spray-drying the feed mixture from step (a) to form a solid dispersion of the pharmaceutical agent and the polymer by introducing the feed mixture as droplets into a spray-drying chamber via an atomizing means.

In one embodiment, the droplets that are introduced into the drying chamber are exposed to a heated drying gas.

In a further aspect, this invention provides a solid dispersion of TMC125 in powder form obtainable by a process specified above or hereinafter.

In still another aspect, there is provided a pharmaceutical formulation comprising a solid dispersion of TMC125 in powder form, prepared or obtainable by the process specified above or hereinafter, and further excipients. The pharmaceutical formulation preferably is converted into a unitary dosage form such as a tablet, capsule, sachet, pill, powder packet, suppository and the like. Hence, the invention further provides a solid dosage form comprising a solid dispersion of TMC125 in powder form as specified above or hereinafter.

The process of this invention yields a solid that has a relatively high density compared with the spray-dried powders without MCC. The density of the solid dispersion of TMC125 produced by the process of the invention may be in the range of about 0.05 g/ml to 1 g/ml, in particular of about 0.1 to 0.7 g/ml.

Without being bound to theory, it is assumed that the microcrystalline cellulose acts as a small internal carrier, which is positioned in the droplets of the feed mixture, from which the solid dispersion of polymer and pharmaceutical agent forms. An advantage of this process is that the solid dispersion of TMC125 produced may be more readily formulated into a dosage form, such as a tablet or capsule, which means that less or even no pre-compacting is needed in a subsequent formulation process. The high density of the solid dispersion of TMC125 gives rise to a reduction in the size of the resulting dosage form, thereby reducing pill burden.

The TMC125 active agent in the solid dispersion produced by the process of the invention is preferably highly amorphous, that is, it has a low level of or no crystallinity. By "amorphous" is meant that the pharmaceutical agent is in a non-crystalline state. An advantage of this is that the bioavailability of the pharmaceutical agent in the resulting solid dispersion and the dosage forms derived therefrom is increased, which has the effect of reducing the amount of active agent that needs to be administered, thereby also reducing pill burden.

Preferably, the degree of crystallinity of the pharmaceutical agent in the solid dispersion of TMC125, as can be characterized by X-ray powder diffraction (XRPD), is about 10% or less, about 9% or less, about 8% or less, about 7% or less, about 6% or less, about 5% or less, about 4% or less, about 3% or less, about 2% or less, about 1% or less, about 0.5% or less, or about 0.1% or less.

The solid dispersion produced by the process of the invention typically comprises particles having an average effective particle size in the range of from about 10 µm to about 150 µm, or about 15 µm to about 100 µm, particularly about 20 µm to about 80 µm, or 30 µm to about 50 µm, preferably about 40 µm. As used herein, the term average effective particle size has its conventional meaning as known to the person skilled in the art and can be measured by art-known particle size measuring techniques such as, for example, sedimentation field flow fractionation, photon correlation spectroscopy, laser diffraction or disk centrifugation. The average effective particle sizes mentioned herein may be related to weight distributions of the particles. In that instance, by "an average effective particle size of about 150 µm" it is meant that at least 50% of the weight of the particles consists of particles having a particle size of less than the effective average of 50 µm, and the same applies to the other effective particle sizes mentioned. In a similar manner, the average effective particle sizes may be related to volume distributions of the particles but usually this will result in the same or about the same value for the average effective particle size.

The so-called "span" of the particles produced by the process of the invention may be lower than about 3, in particular lower than about 2.5, preferably the span is about 2. Usually the span will not be lower than about 1. As used herein the term "span" is defined by the formula $(D_{90}-D_{10})/D_{50}$ wherein $D_{90}$ is the particle diameter corresponding to the diameter of particles that make up 90% of the total weight of all particles of equal or smaller diameter and wherein $D_{50}$ and $D_{10}$ are the diameters for 50 respectively 10% of the total weight of all particles.

As used herein, the term "TMC125" is meant to comprise the base form as well as any pharmaceutically acceptable acid addition salt thereof. The pharmaceutically acceptable addition salts as mentioned hereinabove are meant to comprise the therapeutically active non-toxic acid addition salt forms, which the compound of formula (I) is able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxy-propanoic, 2-oxopropanoic, oxalic, malonic, succinic, maleic, fumaric, malic, tartaric, 2-hydroxy-1,2,3-propanetricarboxylic, methanesulfonic, ethanesulfonic, benzene-sulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The term addition salt also comprises the hydrates and solvent addition forms which the compounds of formula (I) are able to form. Examples of such forms are e.g. hydrates, alcoholates and the like.

The amount of TMC125 in the spray dried product may be in the range from about 10% to about 50%, in particular about 15% to about 40%, or about 20% to about 30% or about 20% to about 25%, by weight relative to the total weight of the spray dried product comprising TMC125, water-soluble polymer, MCC and optional excipients.

The amount of TMC125 in the feed mixture can be calculated based on these percentages and on the amount of solvent used.

The microcrystalline cellulose (MCC) that can be used has an average particle size, which is selected such that when mixed into the solution of pharmaceutical agent and water-soluble polymer, the resulting feed mixture is able to pass through the atomizing means into the spray-drying chamber without clogging or blocking the atomizer. As such, the size of the MCC is limited by the particular size of the atomizing means provided on the spray-drying chamber. For example, where the atomizing means is a nozzle, the size of the nozzle bore will affect the size range of the MCC that may be used. The average particle size of the MCC may be in the range of from 5 µm to 50 µm, in particular from 10 µm to 30 µm, e.g. about 20 µm.

Microcrystalline cellulose that can be used comprises the AVICEL™ series of products available from FMC BioPolymer, in particular AVICEL PH 105™ (20 µm), AVICEL PH 101™ (50 µm), AVICEL PH 301™ (50 µm); the microcrystalline cellulose products available from JRS Pharma, in particular VIVAPUR™ 105 (20 µm), VIVAPUR™ 101 (50 µm), EMCOCEL™ SP 15 (15 µm), EMCOCEL™ 50M 105 (50 µm), PROSOLV™ SMCC 50 (50 µm); the microcrystalline cellulose products available from DMV, in particular PHARMACEL™105 (20 µm), PHARMACEL™101 (50 µm); the microcrystalline cellulose products available from Blanver, in particular TABULOSE (Microcel)™101 (50 µm), TABULOSE (Microcel)™103 (50 µm); the microcrystalline cellulose products available from Asahi Kasei Corporation, such as CEOLUS™ PH-F20JP (20 µm), CEOLUS™ PH-101 (50 µm), CEOLUS™ PH-301 (50 µm), CEOLUS™ KG-802 (50 µm).

A particularly preferred microcrystalline cellulose is AVICEL PH 1050 (20 µm).

The amount of MCC in the spray dried product may be in the range from about 5% to about 25%, in particular about 7.5% to about 20%, or about 10% to about 15% or about 10% to about 12.5%, by weight relative to the total weight of the spray dried product comprising TMC125, water-soluble polymer, MCC and optional excipients. The weight ratio of the amounts of MCC to TMC125 in the spray dried product can be calculated based on these percentages and in particular may be in the range of from about 2:1 to about 1:5, in particular from about 1:1 to 1:7, preferably about 1:2. The amount of MCC in the feed mixture can be calculated based on these percentages and on the amount of solvent used. In view of the desirability of keeping the concentration of pharmaceutical agent in the resulting solid pharmaceutical composition as high as possible, the concentration of MCC is preferably kept as low as possible.

An advantage of using microcrystalline cellulose is that in addition to increasing the density of the resulting solid pharmaceutical composition, it may also function to increase the properties of flowability, compressibility, disintegration and dissolution of the spray-dried solid dispersion of TMC125 and of pharmaceutical compositions derived therefrom.

Water-soluble polymers suitable for use in the process of this invention are pharmaceutically acceptable and substantially unreactive towards the pharmaceutical agent. Suitable polymers include cellulosic polymers, such as methyl cellulose, ethyl cellulose, hydroxymethyl cellulose, hydroxyethyl cellulose, hydroxypropyl cellulose, hydroxybutyl cellulose, hydroxyethylmethyl cellulose, hydroxypropylmethyl cellulose (or HPMC, e.g. HPMC 2910 15 mPa·s; HPMC 2910 5 mPa·s), e.g. HPMC 2910, carboxymethyl cellulose, hydroxypropylmethyl cellulose phthalate (HPMCP), e.g. HP 50, hydroxypropylmethylcellulose acetate succinate (HPMCAS), cellulose acetate trimellitate (CAT), hydroxypropylcellulose acetate phthalate (HPCAP), hydroxy-propylmethyl cellulose acetate phthalate (HPMCAP), methylcellulose acetate phthalate (MCAP) and mixtures thereof such as a mixture of hydroxypropyl cellulose and ethyl cellulose. Suitable polymers also include polyvinyl pyrrolidone, copolyvidone (PVPCoVA, sometimes also referred to as PVP-VA), which is polyvinyl pyrrolidone copolymerised with vinyl acetate, and aminoalkyl methacrylate copolymers, such as Eudragit E® 100 (Röhm GmbH, Germany).

Water-soluble polymers of interest include hydroxypropylmethyl cellulose (HPMC), polyvinyl pyrrolidone or copolyvidone. A particularly preferred hydroxypropylmethyl cellulose is HPMC 2910 5 mPa·s. A particularly preferred polyvinyl pyrrolidone is PVP K12, PVP K29-32 such as PVP K30, PVP K90 and a particularly preferred copolyvidone is PVP-co-VA64 (PVPCoVA, sometimes also referred to as PVP-VA).

In one embodiment, the polymer has a molecular weight in the range 500D to 2 MD. The polymer may have an apparent viscosity of 1 to 15,000 mPa·s when in a 2% aqueous solution at 20° C.

The water-soluble polymers in the solid dispersions particles are polymers that have an apparent viscosity, when dissolved at 20° C. in an aqueous solution at 2% (w/v), of 1 to 5000 mPa·s, in particular of 1 to 700 mPa·s, more in particular of 1 to 100 mPa·s.

Said HPMC contains sufficient hydroxypropyl and methoxy groups to render it water-soluble. HPMC having a methoxy degree of substitution from about 0.8 to about 2.5 and a hydroxypropyl molar substitution from about 0.05 to about 3.0 are generally water-soluble. Methoxy degree of substitution refers to the average number of methyl ether groups present per anhydroglucose unit of the cellulose molecule. Hydroxypropyl molar substitution refers to the average number of moles of propylene oxide that have reacted with each anhydroglucose unit of the cellulose molecule. A preferred HPMC is hypromellose 2910 15 mPa·s or hypromellose 2910 5 mPa·s, especially hypromellose 2910 15 mPa·s. Hydroxypropyl methylcellulose is the United States Adopted Name for hypromellose (see Martindale, The Extra Pharmacopoeia, 29th edition, page 1435). In the four digit number "2910", the first two digits represent the approximate percentage of methoxy groups and the third and fourth digits the approximate percentage composition of hydroxypropoxyl groups; 15 mPa·s or 5 mPa·s is a value indicative of the apparent viscosity of a 2% aqueous solution at 20° C.

Copolymers of vinylpyrrolidone and vinyl acetate that may be used include those copolymers wherein the molecular ratio of the monomers vinylpyrrolidone to vinyl acetate is about 1.2 or wherein the mass ratio of the monomers vinylpyrrolidone to vinyl acetate is about 3:2. Such copolymers are commercially available and are known as copovidone or copolyvidone, sold under trademarks Kolima™ or Kollidon VA 64™. The molecular weight of these polymers may be in the range of about 45 to about 70 kD. The K-value, obtained from viscosity measurements may be in the range of about 25 to about 35, in particular the K value may be about 28.

Polyvinylpyrrolidine polymers that may be used are known as povidone (PVP) and are commercially available. They may have a molecular weight that is in the range of about 30 kD to about 360 kD. Examples are the PVP products sold by BASF under the tradename Kolidon™, e.g. PVP K25 (Mw=29.000), PVP K30 (Mw=40.000), and PVP K90 (Mw=360.000).

The amount of water-soluble polymer in the spray dried product may be in the range from about 30% to about 75%, in particular about 40% to about 75%, or about 50% to about 75% or about 60% to about 70%, by weight relative to the total weight of the spray dried product comprising TMC125, water-soluble polymer, MCC and optional excipients. The amount of water-soluble polymer in the feed mixture can be calculated based on these percentages and on the amount of solvent used.

Typically, the weight:weight ratio of water-soluble polymer to TMC125 is in the range from about 10:1 to about 1:10, in particular from about 10:1 to about 1:1, more in particular from about 5:1 to about 1:1, preferably from about 3:1 to about 1:1, e.g. a ratio of about 3:1. The ratio of water-soluble polymer to pharmaceutical agent is believed to affect the degree of crystallinity of the pharmaceutical agent in the resulting solid pharmaceutical composition. However, it is also desirable to reduce the amount of polymer in relation to the pharmaceutical agent in order to maximize the amount of pharmaceutical agent in the resulting pharmaceutical composition.

The solvent used in the process of the invention may be any solvent, which is inert with respect to TMC125 and which is able to dissolve TMC125 and the water-soluble polymer, but which does not dissolve the MCC. Suitable solvents include acetone, tetrahydrofuran (THF), dichloromethane, ethanol (anhydrous or aqueous), methanol and combinations thereof. Where the polymer is HPMC, the solvent is preferably a mixture of dichloromethane and ethanol, more preferably a mixture of dichloromethane and ethanol, the latter in particular being anhydrous ethanol, in a 9:1 ratio by weight. Where the polymer is polyvinyl pyrrolidone or copolyvidone, the solvent is preferably acetone. The amount of solvent present in the feed mixture will be such that TMC125 and the water-soluble polymer are dissolved and that the feed mixture has sufficient low viscosity for it to be sprayed. In one embodiment the amount of solvent in the feed mixture will be at least 80%, in particular at least 90%, preferably at least 95%, the percentages expressing the weight amount of solvent to the total weight of the feed mixture.

Examples of feed mixtures that can be used in the process of the invention are those comprising:
(i) 200 mg TMC125, 200 mg HPMC 2910 5 mPa·s, 100 mg microcrystalline cellulose (AVICEL PH 1050) in 14.57 g dichloromethane extra pure and 1.619 g ethanol 96% (v/v);
(ii) 200 mg TMC125, 400 mg HPMC 2910 5 mPa·s, 100 mg microcrystalline cellulose (AVICEL PH 1050) in 14.57 g dichloromethane extra pure and 1.619 g ethanol 96% (v/v);
(iii) 200 mg TMC125, 600 mg HPMC 2910 5 mPa·s, 100 mg microcrystalline cellulose (AVICEL PH 1050) in 14.57 g dichloromethane extra pure and 1.619 g ethanol 96% (v/v);
(iv) 222 mg TMC125, 667 mg HPMC 2910 5 mPa·s, 111 mg microcrystalline cellulose (AVICEL PH 1050) in 16.19 g dichloromethane extra pure and 1.8 g ethanol absolute.

The above feed mixtures can be scaled up by multiplying the quantities mentioned by a factor that is in the range of about 1 to about $10^5$. In lab scale production the quantities may be multiplied by a factor in the range of about 1 to about 1000. For medium or large scale production this factor may be in the range of about 500 to about $10^5$, e.g. about $10^3$, about $2.10^3$, about $5.10^3$ or about $10^4$.

The solvent is removed from the droplets of the feed mixture by the spray-drying step. Preferably the solvent is volatile, with a boiling point of 150° C. or less, preferably 100° C. or less. The solvent should be substantially completely removed from the droplets of the feed mixture during the spray-drying step.

The drying gas may be any gas. Preferably, the gas is air or an inert gas such as nitrogen, nitrogen-enriched air or argon. The temperature of the drying gas at the gas inlet of the spray-drying chamber is typically from about 60° C. to about 300° C.

Suitable spray dryers include Niro pharmaceutical spray dryer models such as Mobile Minor, PSD-1, PSD-2, PSD-3, PSD-4, and SD-12.5-N (Niro A/S, Soeburg, Denmark) or a Büchi P290 or P190.

A typical spray-drying apparatus for use in the process of this invention comprises a spray-drying chamber, atomizing means for introducing the feed mixture into the spray-drying chamber in the form of droplets, a source of heated drying gas that flows into the spray-drying chamber through an inlet, and an outlet for the heated drying gas. The spray-drying apparatus also comprises a means for collecting the solid pharmaceutical powder that is produced.

The spray-drying apparatus may have a closed or an open cycle configuration, in which the heated drying gas leaving the outlet is fed back, respectively not fed back, into the chamber. Alternatively, the spray-drying apparatus may also have a closed cycle configuration, in which the organic solvent is recycled. The closed cycle configuration is preferable for economic but in particular for environmental reasons.

The atomizing means preferably comprises a rotary atomizer, a pneumatic nozzle or a high pressure nozzle, which is able to atomize the feed mixture into the spray-drying chamber so that droplets of feed mixture are produced having a particular droplet size range. The atomizing means is preferably a high-pressure nozzle.

Suitable rotary atomizers include those having an air turbine drive operating from a high pressure compressed air source, for example a 6 bar compressed air source, which supplies power to an atomization wheel for atomizing the feed mixture. The atomization wheel may be vaned. Preferably, the rotary atomizer is located in the upper part of the spray-drying chamber, for example in the chamber roof, so that the droplets produced dry and fall to the lower part of the chamber. Typically, rotary atomizers produce droplets which, have a size in the range of from about 20 to about 225 μm, in particular from about 40 to about 120 μm, the particle size being dependent upon the wheel peripheral velocity.

Suitable pneumatic nozzles (which include two-fluid nozzles) comprise those that are located in the upper part of the spray-drying chamber, for example in the chamber roof, and operate in so-called "co-current mode". Atomization takes place using compressed air such that the air-liquid ratio is in the range of about 0.5-1.0:1 to about 5:1, in particular from about 1:1 to about 3:1. The feed mixture and the atomizing gas are passed separately to the nozzle head, where the atomization takes place. The size of the droplets produced by pneumatic nozzles depends on the operating parameters and can be in the range from about 5 to 125 μm, in particular from about 20 to 50 μm.

Two-fluid nozzles that operate in so-called "counter-current mode" may also be used in the process of the present invention. These nozzles operate in a similar way to two-fluid nozzles in co-current modes except that they are located in a lower part of the drying chamber and spray droplets upwards. Typically, counter-current two-fluid nozzles generate droplets which, when dried, produce particles having a size in the range of from about 15 to about 80 μm. Two-fluid nozzles in counter-current mode are particularly useful where the components of the solid pharmaceutical powder are not heat sensitive, since the residence time of the droplets/powder in the spray-drying chamber is generally longer than in co-current mode.

A preferred atomizer type for use in the invention is the high pressure nozzle where liquid feed is pumped to the nozzle under pressure. Pressure energy is converted to kinetic energy, and feed issues from the nozzle orifice as a high speed film that readily disintegrates into a spray as the film is unstable. The feed is made to rotate within the nozzle using a swirl insert or swirl chamber resulting in cone shaped spray patterns emerging from the nozzle orifice. Swirl insert, swirl chamber and orifice dimensions together with variation of pressure gives control over feed rate and spray characteristics. The size of the droplets produced by high pressure nozzles depends on the operating parameters and can be in the range from about 5 to 125 μm, in particular from about 20 to 50 μm.

Suitable atomizing means for use in the process of the invention may be selected depending on the desired droplet size. The latter depends upon a number of factors, such as the viscosity and temperature of the feed mixture, the desired flow rate and the maximum acceptable pressure to pump the feed mixture. As such, the atomizing means is selected so that the desired average droplet size may be obtained for a feed mixture having a particular viscosity and which is admitted to the spray-drying chamber at a particular flow rate. Generally, if the nozzle is too large it will deliver too large a droplet size when operated at the desired flow rate, and this effect is amplified the higher the viscosity of the feed mixture. A problem with very large droplets is that the rate of solvent evaporation tends to be slower, which can lead to the formation of product having more highly crystalline pharmaceutical agent. On the other hand, use of a nozzle that is too small may require an unacceptably high pressure to pump the feed mixture into the spray-drying chamber at an acceptable flow rate.

Various spray-drying parameters, such as the temperature of the heated drying gas, the drying gas flow rate, the relative humidity of the drying gas, the atomizing pressure, the nozzle bore diameter size, and the rate of introduction of the feed mixture to the spray-drying chamber, may influence properties such as the yield of the pharmaceutical powder, the amount of residual solvent, as well as the droplet size. These parameters can be optimized depending on the particular spray-drying chamber being used in order to obtain spray-dried powders having the desired properties.

Optionally, further excipients may be included in the feed mixture. Such excipients may be included in order to improve properties of the feed mixture or the resulting solid pharmaceutical composition, such as handling or processing properties. Regardless of whether or not excipients are added to the feed mixture, which obviously results in them being incorporated in the spray-dried solid dispersion, excipients may also be mixed with the resulting solid spray-dried dispersion during formulation into a desired dosage form. The spray-dried solid dispersion may be subjected to further processing steps depending on the nature of the final dosage form. For example, the pharmaceutical composition may be subjected to a post-drying process, or may undergo slugging or roller compacting prior to tabletting or encapsulating.

The spray-dried solid dispersion produced using the process of the invention may be formulated into a pharmaceutical formulation. The latter comprises the spray-dried solid dispersion produced by the process of the invention and a carrier, which may comprise one or more pharmaceutically acceptable excipients. The latter include surfactants, solubilizers, disintegrants, pigments, flavourings, fillers, lubricants, glidants, preservatives, thickening agents, buffering agents and pH modifiers. Typical surfactants include sodium lauryl sulphate, Cremophor RH 40, Vitamin E TPGS and polysorbates, such as Tween 20™. Typical pH modifiers are acids, such as citric acid or succinic acid, bases or buffers.

The pharmaceutical formulations in turn may be converted into an appropriate dosage form. Typical dosage forms include dosage forms for oral administration, such as tablets, capsules, suspensions and pastilles, and dosage forms for rectal or vaginal administration, such as gels, suppositories or pastes. Depending on whether the dosage form is intended for immediate release or controlled release, further processing steps may be required, such as the incorporation of a disintegrant for immediate release products or the coating of the dosage form with an enteric layer for controlled release products. Suitable disintegrants include microcrystalline cellulose, starch, sodium starch glycolate, and crosslinked carboxy methyl cellulose sodium, crosslinked PVP.

This invention also relates to a solid pharmaceutical powder, or, to a spray-dried powder, comprising microcrystalline cellulose in a solid dispersion of the anti-HIV compound etravirine (TMC125) in a water-soluble polymer. The invention further provides a pharmaceutical formulation or a pharmaceutical dosage form containing a solid pharmaceutical powder, or, a spray-dried powder, comprising microcrystalline cellulose in a solid dispersion of the anti-HIV compound etravirine (TMC125) in a water-soluble polymer.

As used herein, the word "substantially" does not exclude "completely" e.g. a composition which is "substantially free" from Y may be completely free from Y. Where necessary, the word "substantially" may be omitted from the definition of the invention. The term "about" in connection with a numerical value is meant to have its usual meaning in the context of the numerical value. Where necessary the word "about" may be replaced by the numerical value ±10%, or ±5%, or ±2%, or ±1%. All documents cited herein are incorporated by reference in their entirety.

EXAMPLE

1) Manufacturing of Spray-Dried Powders With and Without MCC

TMC 125:HPMC (1:3)

The feed mixture of the formulation without MCC contained 8.64 kg TMC125, 25.0 kg HPMC 2910 5 mPa·s, in 540 kg dichloromethane and 60 kg ethanol absolute (99.9%). This feed mixture was then admitted to a SD-12.5-N, closed cycle spray-drying chamber via a high-pressure nozzle in co-current mode under the conditions shown in table below.

| Spray-drying parameters | |
|---|---|
| Drying gas | Nitrogen |
| Nozzle diameter (mm) | 1.4 SF |
| Atomizing pressure (bar) | 23 |
| Feed rate (kg/h) | 202 |
| Drying gas flow rate (kg/h) | 1250 |
| Inlet temperature of drying gas (° C.) | 115 |
| Outlet temperature of drying gas (° C.) | 49 |
| Condenser temperature | −12° C. |

The resulting solid pharmaceutical composition was collected from the cyclone, post-dried under vacuum at elevated temperature to decrease the residual solvent level. The dried powder was sieved and the powder fraction with a particle size between 45 and 100 µm was retained and subsequently subjected to dissolution testing.

TMC 125:HPMC:MCC (1:3:0.5)

| Spray-drying parameters | |
|---|---|
| Drying gas | Nitrogen |
| Nozzle diameter (mm) | 1.5 |
| Atomizing pressure (bar) | 40 |
| Feed rate (kg/h) | 190-210 |
| Drying gas flow rate (kg/h) | 1250 |
| Inlet temperature of drying gas (° C.) | 113 |
| Outlet temperature of drying gas (° C.) | 50 |
| Condenser temperature | −11° C. |

Feed mixtures for the spray-dried formulations were prepared by dissolving TMC125 and the polymer in the solvent and adding microcrystalline cellulose. The polymer-type, solvent and the amounts of the components used are listed under the fourth preferred feed mentioned hereinabove. The feed mixture was then admitted to a SD-12.5-N, closed cycle spray-drying chamber via a high-pressure nozzle in co-current mode under the conditions shown in table above. The resulting solid pharmaceutical composition was collected from the cyclone, post-dried under vacuum at elevated temperature to decrease the residual solvent level. The dried powder was sieved and the powder fraction with a particle size between 45 and 100 µm was retained and subsequently subjected to dissolution testing.

2) Description of Dissolution Test+HPLC Analysis 2.1) Dissolution Testing

Sample weight taken: 200 mg

Dissolution medium: 750 ml FeSSIF+250 ml 0.01M HCl

Dissolution method: 100 RPM, sample collected every 5 min, run time 180 min

Temperature: 37° C.

Preparation of Fasted State Simulated Intestinal Fluid (FaSSIF)

Fassif, containing 3 mmol/l sodium taurocholate (NaTC) and 0.75 mmol/l Lecithin, with a pH of 6.50 and an osmolality of 270 mosmol/kg, was prepared as follows:

Preparation of Blank FaSSIF:

Dissolve 1.74 g of NaOH (pellets), 19.77 g of $NaH_2PO_4 \cdot H_2O$ (or 17.19 g of anhydrous $NaH_2PO_4$) and 30.93 g of NaCl in 5 l of deionized water. Adjust the pH to exactly 6.5 using 1 N NaOH or 1 N HCl.

Preparation of FaSSIF:

1. Dissolve 3.3 g* of sodium taurocholate (NaTC) in 500 ml blank FaSSIF.
2. Dissolve 1.18 g* of Lecithin in approximately 12 ml* methylene chloride.
3. The Lecithin solution was added to the sodium taurocholate solution, forming an emulsion.
4. The methylene chloride was removed under vacuum at 40° C. (e.g. using a ratovapor). Care was taken to avoid foam coming out of the rotavapor-flask by gradually building up the vacuum. This resulted in an almost clear micellar solution, having no perceptible odor of methylene chloride.
5. After cooling to room temperature, the volume was adjusted to 2l with blank FaSSIF.

For preparation of larger volumes of FaSSIF (up to 6 l), it is possible to multiply the amount of NaTC and still dissolve this in 500 ml blank FaSSIF. The amounts of lecithin and methylene chloride is adjusted accordingly.

2.2) HPLC Analysis

Column: 50*3 mm id, Xterra MS-C18, 5 Mm particle size

Elution mode: Isocratic

Flow rate: 0.5 ml/min

Mobile phase: 35% A and 65% B

A: phosphoric acid 0.5%

B: acetonitrile

Detection: UV at 260 nm

Injection volume: 100 µl.

Run time: 3 min

Column temperature: 35° C.

0.1 ml of filtered sample was collected from the dissolution medium and diluted in 0.9 ml of 35/65 phosphoric acid (0.5%)/acetonitrile. The sample was then directly injected and analysed. All samples were analysed in duplicate to check for reproducibility. For each analysis, two standards were made in the concentration between 20 µl to 25 µl range and analysed in duplicate. The AUC data from HPLC were collected and calculated and plotted in Microsoft Excel.

3) Dissolution Results

Figure 1:
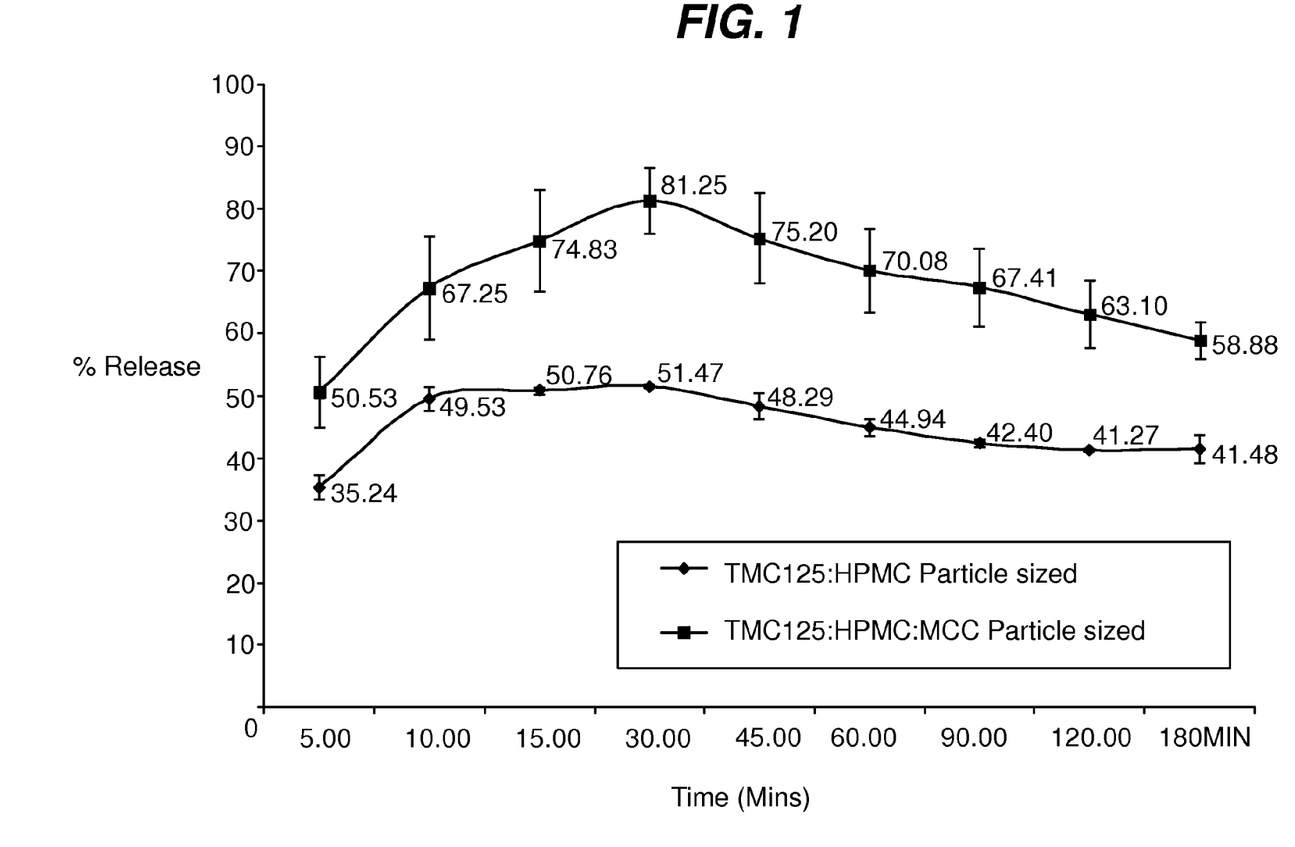
FIG. 1: The resulting dissolution release kinetics of the two size fractioned samples, namely TMC 125:HPMC (1:3) particle size fractioned (45<x<100 μm) and TMC 125:HPMC:MCC (1:3:0.5) particle size fractioned (45<x<100 μm).
Figure 2:
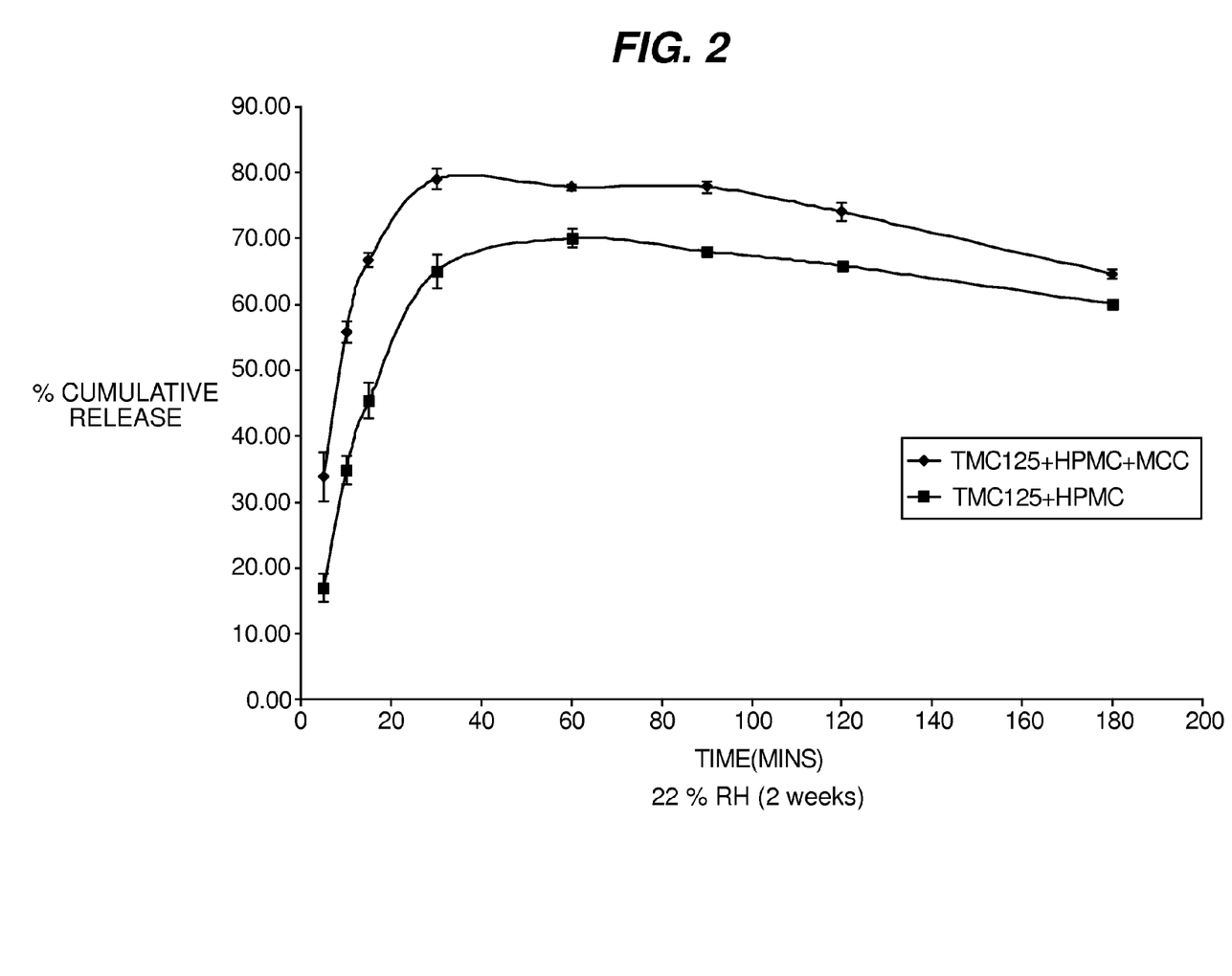
FIGS. 2-9: Dissolution profiles obtained for samples of TMC125:HPMC (1:3) and TMC125:HPMC:MCC (1:3:0.5) (dried) after stability storage at various relative humidities for 2 weeks and for 4 weeks.
Figure 3:
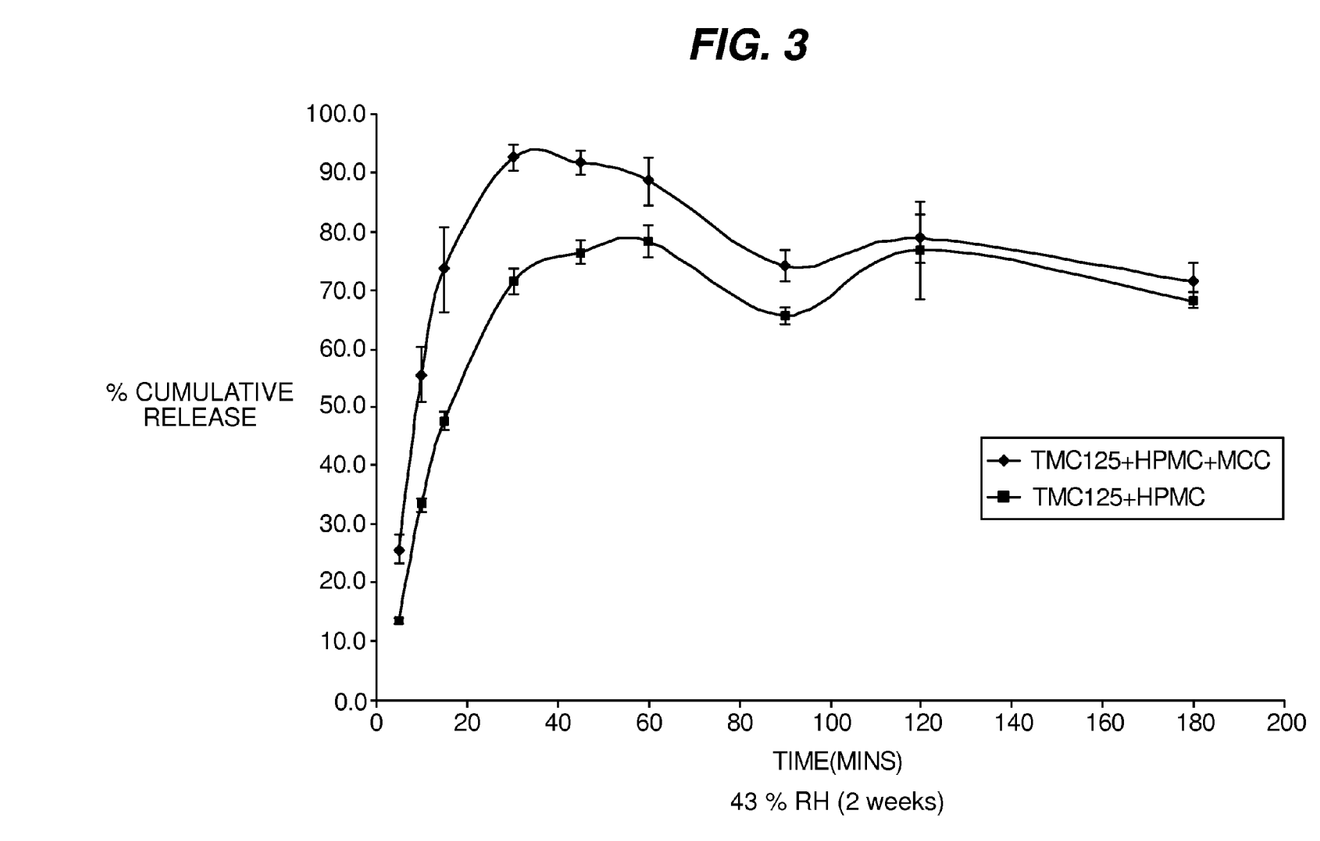
Figure 4:
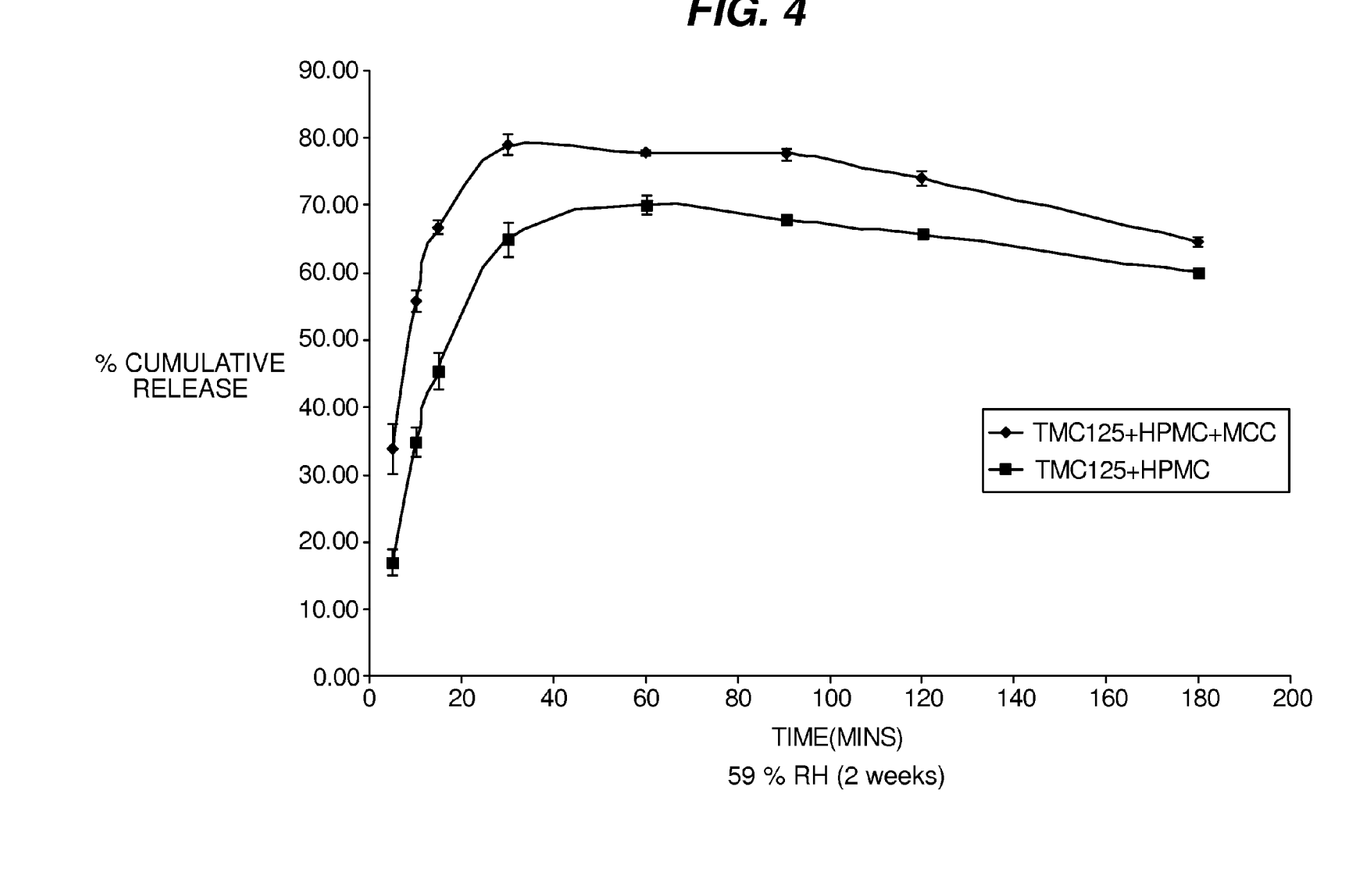
Figure 5:
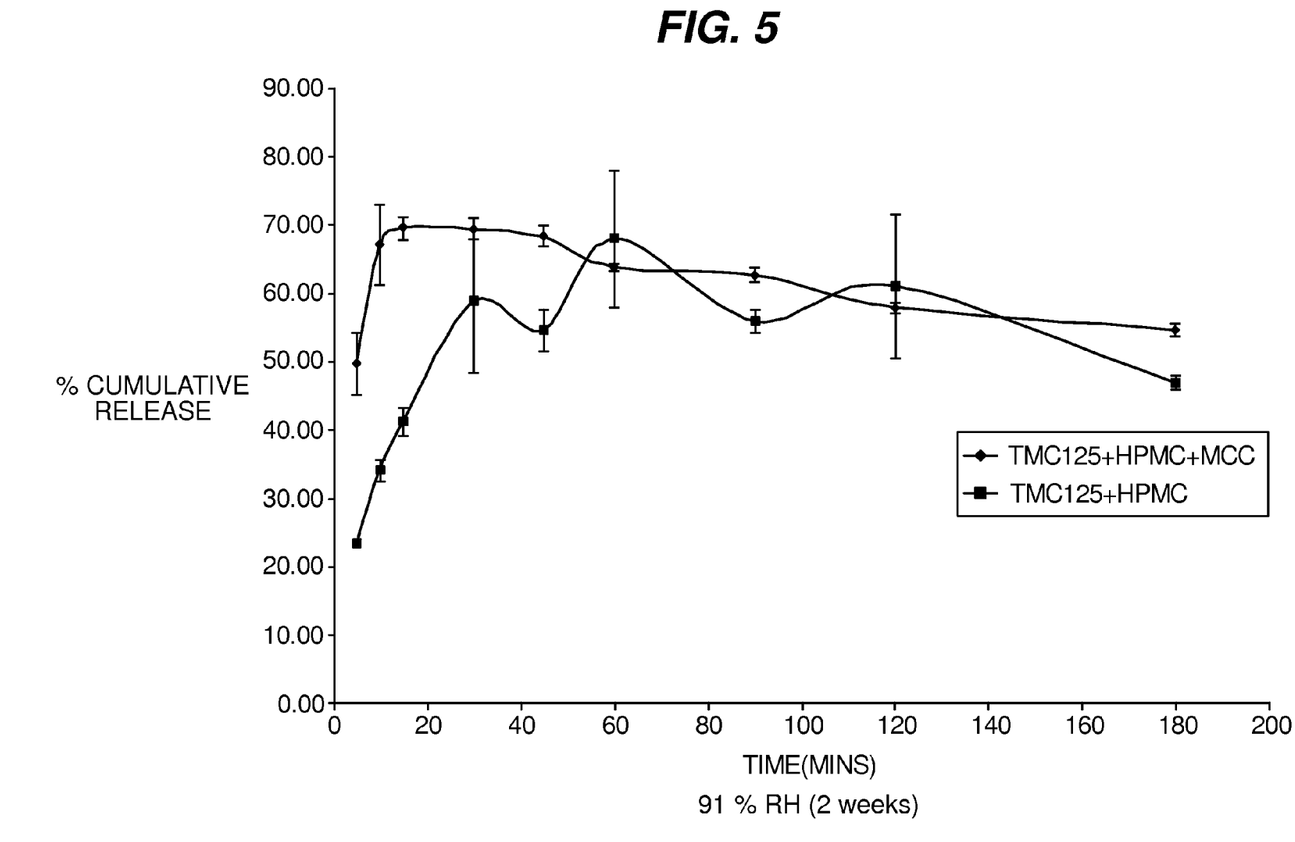
Figure 6:
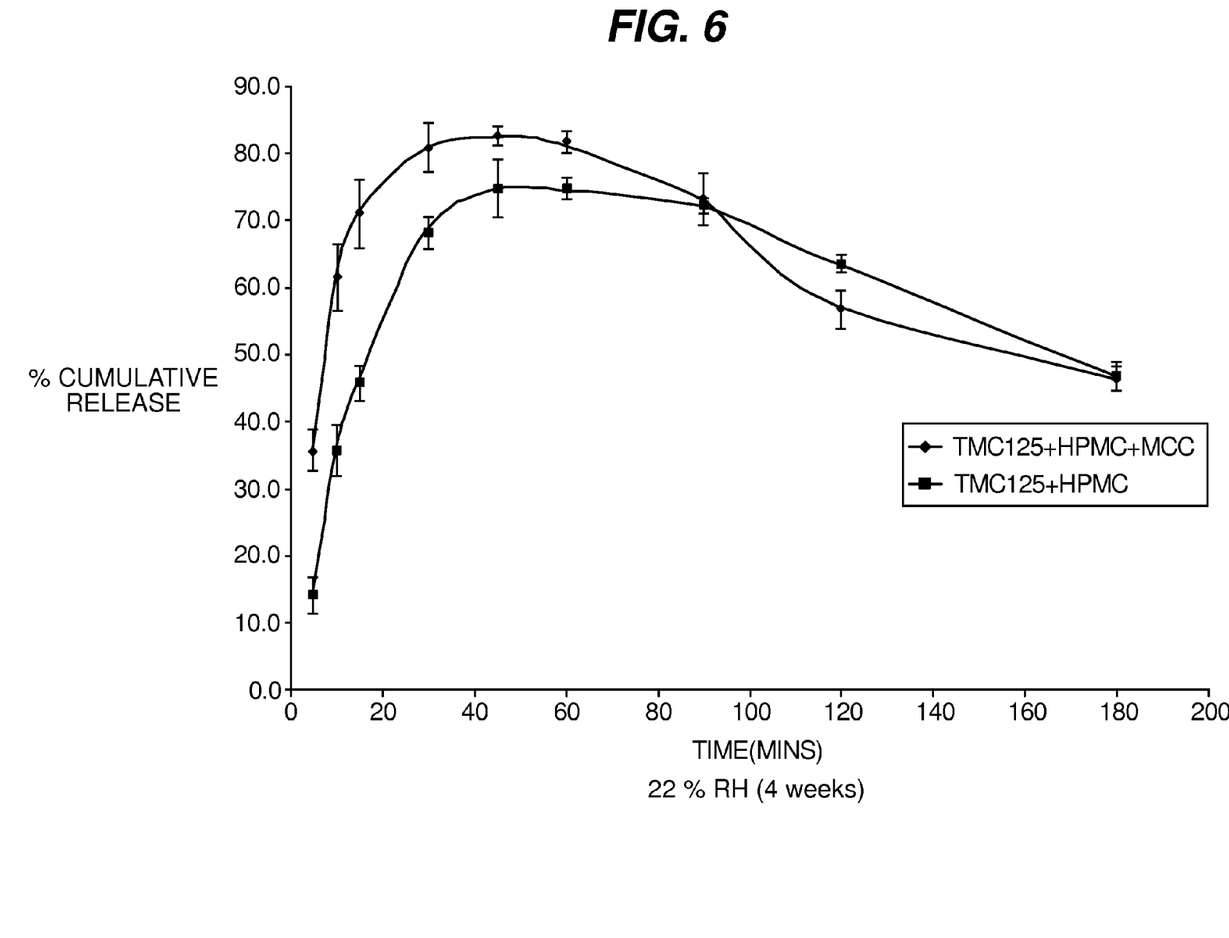
Figure 7:
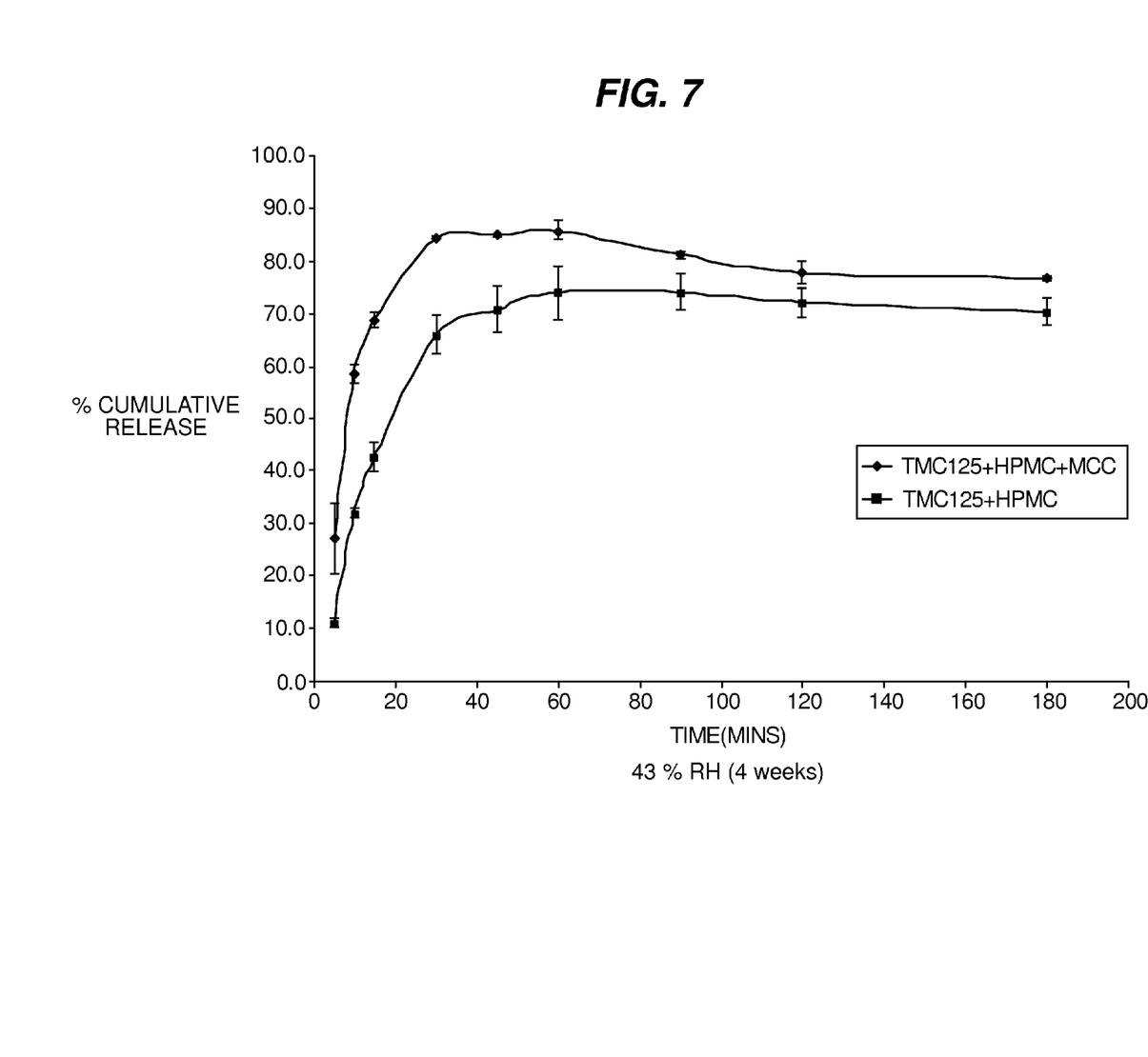
Figure 8:
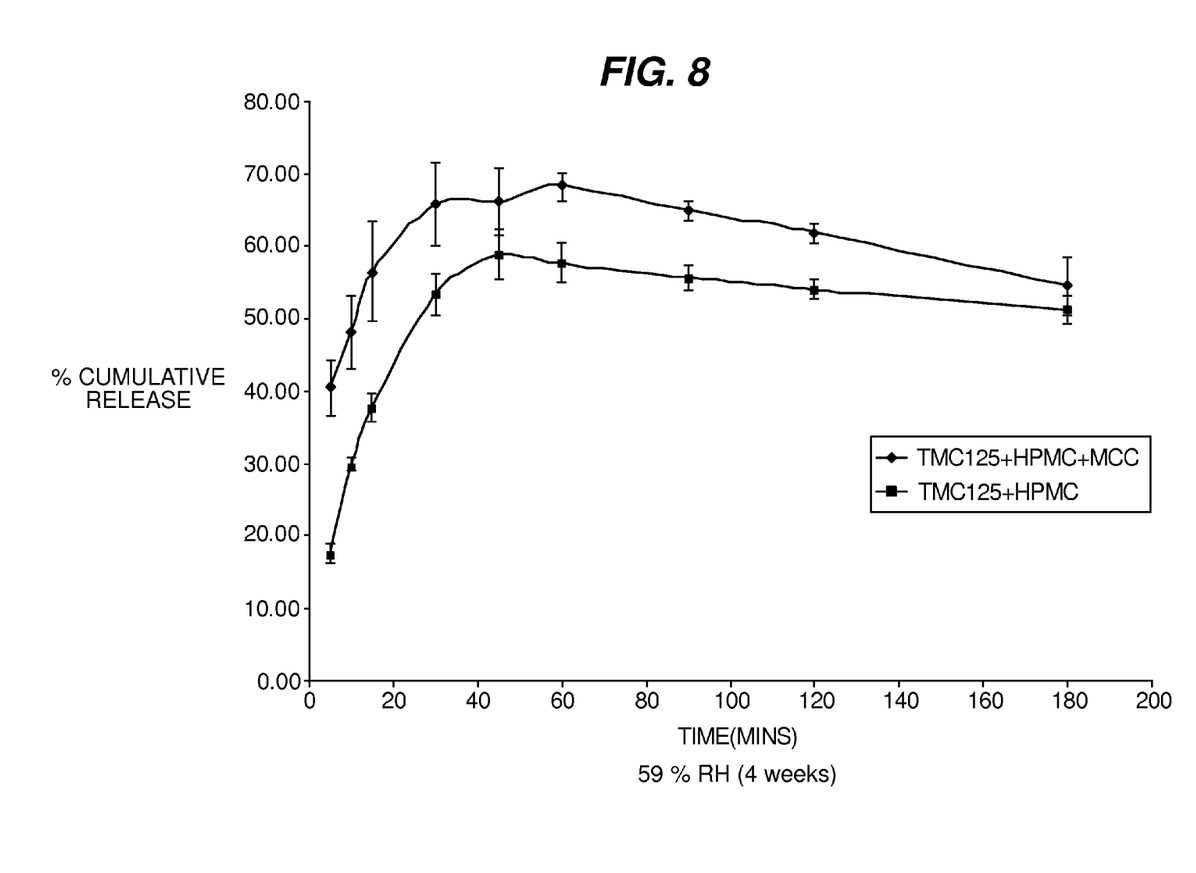
Figure 9:
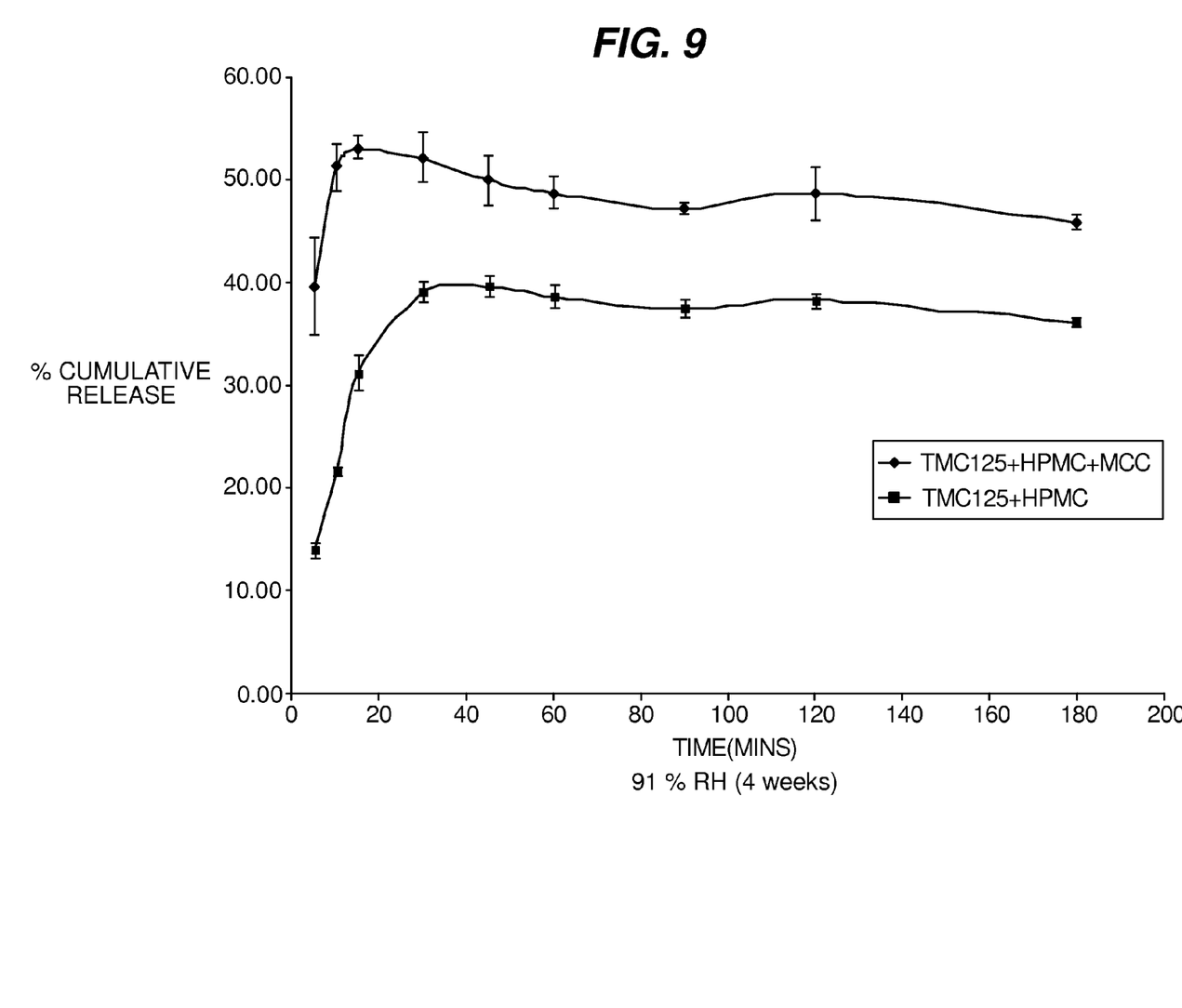

The dissolution results in FIG. 1 were obtained from a dissolution test with spray dried powder immediately after preparation (no storage).

"TMC" in FIG. 1 refers to TMC125.

From the dissolution profiles shown in FIG. 1, it can be seen that the overall rate of dissolution is significantly faster with the formulation containing MCC, compared to that of the non-MCC containing formation. This is also accompanied by an increase in the % release$_{max}$.

4) Stability of Spray-Dried Powders With and Without MCC

Approximately 300 mg of each formulation (TMC 125:HPMC (1:3) and TMC 125:HPMC:MCC (1:3:0.5) was loaded into a 10 ml ampoule and loaded into a desiccator containing a saturated salt solution at 25° C. in order to provide the following relative humidity atmospheres:

22% RH
43% RH
59% RH
91% RH

Prior to loading, the desiccators were left for 48 hours to allow for equilibration. At the respective time points, the individual samples were removed from the desiccators and examined using powder x-ray diffraction (to determine the crystalline nature) as well as dissolution testing to examine the release kinetics of the active from the polymer matrix.

Although for both formulated samples stored at elevated RH, a significant decrease in the % release$_{max}$ was seen after 2 weeks storage, the dissolution profile of the MCC-containing formulation was always higher than the profile of the non-MCC containing formulation. This indicates that the positive effect of the MCC was still present during stress stability conditions.

The invention claimed is:

1. A process for producing a solid pharmaceutical powder, comprising the steps of:
    (a) providing a feed mixture of microcrystalline cellulose (MCC) and a solution of hydroxypropylmethyl cellulose (HPMC) and 4-[[6-amino-5-bromo-2-[(4-cyanophenyl)amino]-4-pyrimidinyl]oxy]-3,5-dimethylbenzonitrile (TMC 125), or a pharmaceutically acceptable acid addition salt thereof, in a solvent; wherein the weight ratio of MCC:HPMC:TMC 125 is 0.5:3:1; and
    (b) spray-drying the feed mixture from step (a) by introducing the feed mixture as droplets into a spray-drying chamber via an atomizing means to form a solid dispersion of amorphous 4-[[6-amino-5-bromo-2-[(4-cyanophenyl)amino]-4-pyrimidinyl]oxy]-3,5-dimethylbenzonitrile or a pharmaceutically acceptable acid addition salt thereof, the hydroxypropylmethyl cellulose, and the microcrystalline cellulose;
    wherein the solid dispersion has a density of about 0.1 to 0.7 g/ml.

2. The process of claim 1, wherein 4-[[6-amino-5-bromo-2-[(4-cyanophenyl)amino]-4-pyrimidinyl]oxy]-3,5-dimethylbenzonitrile base is used.

3. The process of claim 1, wherein the microcrystalline cellulose has an average particle size of 5-50 μm.

4. The process of claim 1, wherein the microcrystalline cellulose has an average particle size of 10-30 μm.

5. The process of claim 1 wherein the microcrystalline cellulose has an average particle size of 20 μm.

6. The process of claim 1, wherein the solvent is selected from the group consisting of acetone, dichloromethane, ethanol, methanol and combinations thereof.

7. The process of claim 1, wherein the atomizing means comprises a high-pressure nozzle.

8. The process of claim 1, wherein the 4-[[6-amino-5-bromo-2-[(4-cyanophenyl)amino]-4-pyrimidinyl]oxy]-3,5-dimethylbenzonitrile, or a pharmaceutically acceptable acid addition salt thereof, in the solid dispersion has a crystallinity of about 10% or less, as characterized by X-ray powder diffraction.

9. The process of claim 1, wherein the atomizing pressure of the spray drying step is about 40 bar.

* * * * *